United States Patent
Nishijima et al.

(10) Patent No.: US 9,523,632 B2
(45) Date of Patent: Dec. 20, 2016

(54) PARTICULATE MATTER SENSOR AND METHOD FOR MANUFACTURING PARTICULATE MATTER SENSOR

(75) Inventors: Hiroki Nishijima, Shizuoka-ken (JP); Tatsuhiro Hashida, Susono (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 0 days.

(21) Appl. No.: 14/234,544

(22) PCT Filed: Aug. 29, 2011

(86) PCT No.: PCT/JP2011/069471
§ 371 (c)(1),
(2), (4) Date: Mar. 12, 2014

(87) PCT Pub. No.: WO2013/030930
PCT Pub. Date: Mar. 7, 2013

(65) Prior Publication Data
US 2014/0245815 A1    Sep. 4, 2014

(51) Int. Cl.
G01N 15/06    (2006.01)
G01N 15/00    (2006.01)
G01M 15/10    (2006.01)

(52) U.S. Cl.
CPC ...... *G01N 15/0656* (2013.01); *G01N 15/0606* (2013.01); *F01N 2560/05* (2013.01); *G01M 15/102* (2013.01); *G01N 2015/0046* (2013.01)

(58) Field of Classification Search
CPC ................... G01N 15/0656; G01N 15/0606
(Continued)

(56) References Cited

U.S. PATENT DOCUMENTS 6,686,263 B1 * 2/2004 Lopatin .............. H01L 51/0021
  438/257
8,608,919 B2 * 12/2013 Bratov ............. G01N 33/54306
  204/403.01

(Continued)

FOREIGN PATENT DOCUMENTS

JP    H1-131443    5/1989
JP    2-48055      10/1990
(Continued)

OTHER PUBLICATIONS

Extended European Search Report issued on Jan. 30, 2015 in European Patent Application No. 11871628.1.
(Continued)

*Primary Examiner* — Peter Macchiarolo
*Assistant Examiner* — Nathaniel Kolb
(74) *Attorney, Agent, or Firm* — Oblon, McClelland, Maier & Neustadt, L.L.P.

(57) ABSTRACT

A particulate matter sensor comprises an insulating body and a pair of electrodes disposed apart form each other on a main surface of the insulating body. The insulating body includes an insulating portion being equal to or higher than the height of the pair of the electrodes in a direction perpendicular to the main surface, formed on the part where the pair of the electrodes are. In one of the methods for manufacturing the particulate matter sensor, first, an electrode pattern composed of a material for the pair of the electrodes is formed on a body material composing the insulating body, and a mask, having identical pattern of the electrode pattern and composed of material which vaporizes at a temperature equal to or lower than a temperature that the electrode pattern is sintered, is formed on the electrode pattern. A thin film of the material composing the insulating portion is
(Continued)

formed, and the electrode pattern and the thin film is sintered to form the electrodes and the insulating portion.

4 Claims, 3 Drawing Sheets

(58) Field of Classification Search
USPC .................................. 73/23.31, 23.33, 28.01
See application file for complete search history.

(56) References Cited

U.S. PATENT DOCUMENTS

| 2007/0218534 | A1* | 9/2007 | Klenerman | C07K 1/14 |
| | | | | 435/173.7 |
| 2009/0217737 | A1 | 9/2009 | Dorfmueller et al. | |
| 2009/0324999 | A1* | 12/2009 | Devoe | H01M 8/0202 |
| | | | | 429/469 |
| 2010/0193378 | A1* | 8/2010 | Bratov | G01N 33/54306 |
| | | | | 205/792 |
| 2011/0081276 | A1 | 4/2011 | Teranishi et al. | |
| 2011/0259079 | A1* | 10/2011 | Maeda | G01N 15/0656 |
| | | | | 73/23.33 |
| 2011/0315654 | A1* | 12/2011 | Vanhelmont | H03H 3/04 |
| | | | | 216/13 |

FOREIGN PATENT DOCUMENTS

| JP | H3-505785 | | 12/1991 |
| JP | 2008-51715 | | 3/2008 |
| JP | 2008051715 A | * | 3/2008 |
| JP | 2009-144577 | | 7/2009 |
| JP | 2011-80781 | | 4/2011 |
| JP | 2011-80926 | | 4/2011 |

OTHER PUBLICATIONS

International Search Report issued Nov. 29, 2011, in PCT/JP2011/069471, filed Aug. 29, 2011.

* cited by examiner

PARTICULATE MATTER SENSOR AND METHOD FOR MANUFACTURING PARTICULATE MATTER SENSOR

TECHNICAL FIELD

The present invention relates to a particulate matter sensor and a method for manufacturing thereof. More specifically, the present invention relates to a particulate matter sensor to output electrical properties in accordance with the amount of particulate matter in a gas to be measured and a method for manufacturing thereof.

BACKGROUND ART

A PM sensor (particulate matter sensor) for detecting the amount of particulate matter (hereinafter, referred to as PM) in an exhaust passage of an internal combustion engine is installed in a system, for instance, in Patent Document 1. The PM sensor includes an insulating substrate, and a pair of electrodes which is disposed on the insulating substrate and positioned apart from each other. If PM in exhaust gas deposit between the pair of the electrodes, conductive property between the electrodes changes with the amount of PM depositing, thereby changing resistance between the electrodes.

Moreover, in technique of Patent Document 1, the PM sensor is disposed downstream of a filter for trapping particulate matter. Therefore, the amount of PM depositing on the electrodes of the PM sensor is related to the amount of PM included in exhaust gas downstream of the filter for trapping particulate matter. In Patent Document 1, a defect of the filter for trapping particulate matter is detected based on the resistance between the electrodes of the PM sensor.

PRIOR ART LITERATURE

Patent Document

Patent Document 1: JP-2009-144577-A

SUMMARY OF THE INVENTION

Problem to be Solved by the Invention

PM in exhaust gas irregularly includes a small amount of PM of large particle size. If the PM of large particle size deposits on the electrodes of the PM sensor, the conductive property between the electrodes drastically changes. As a result, an output of the PM sensor may become less correlation with the real amount of PM depositing. More specifically, by adhesion of the PM of large particle size, the PM sensor may produce a different output from the real amount of PM, and variability of the sensor output may increase.

The present invention aims to solve the above-described problem and provides a PM sensor and a method for manufacturing thereof, of which variability of output is decreased by preventing PM of large particle size from adhering between electrodes.

Means for Solving the Problem

In accomplishing the above object, according to a first aspect of the present invention, there is provided a particulate matter sensor for detecting among of particulate matter in a gas to be measured, the particulate matter sensor including: an insulating body; and a pair of electrodes which is disposed on a main surface of the insulating body and positioned apart from each other; wherein the insulating body includes, on a part where the pair of the electrodes is not formed, an insulating portion being equal to or higher than the pair of the electrodes in a direction perpendicular to the main surface of the insulating body.

According to a second aspect of the present invention, there is provided a method for manufacturing the particulate matter sensor according to claim 1, the method comprising: forming an electrode pattern composed of material for the pair of the electrodes on a base material composing the insulating body; forming, after forming the electrode pattern, on the electrode pattern, a mask having identical pattern of the electrode pattern and composed of material which vaporizes at a temperature equal to or lower than a temperature that the electrode pattern is sintered; forming a thin film composed of material for the insulating portion on the mask and the base material; sintering the electrode pattern and the thin film to form the electrodes and the insulating portion.

According to a third aspect of the present invention, there is provided a method for manufacturing the particulate matter sensor according to claim 1, the method comprising: forming a trench having identical configuration of pattern of the pair of the electrodes on a base material composing the insulating body; forming the pair of the electrodes on bottom of the trench.

Effects of the Invention

According to the present invention, the insulating portion having height equal to or higher than the electrodes is formed between the electrodes of the particulate matter sensor. When particulate matters (PM) of large particle size are included in exhaust gas, PM is easy to deposit on the electrodes and is hard to deposit between the electrodes because PM is blocked by the insulating portion between the electrodes. Therefore, drastic variation of conductive property between the electrodes is suppressed by adhesion of PM of large particle size and variability of the sensor output is decreased.

MODES FOR CARRYING OUT THE INVENTION

Figure 1:
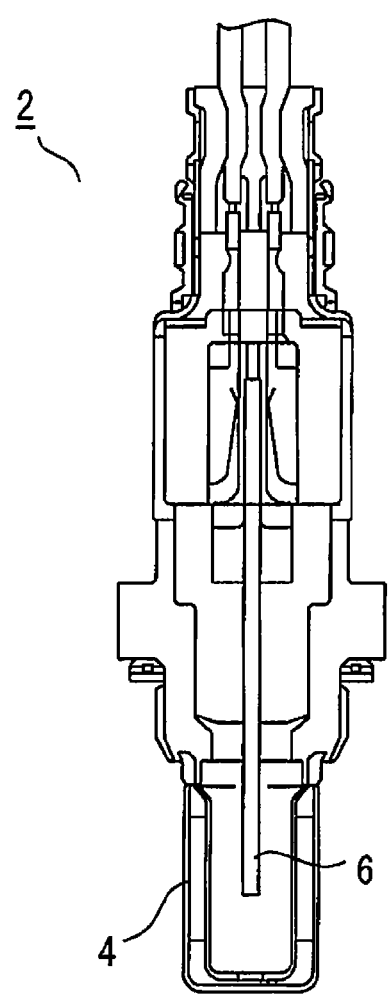
FIG. 1 is a diagram illustrating the overall configuration of a PM sensor according to the present embodiment of the present invention.

An embodiment of the present invention will now be described with reference to the accompanying drawings. For each of the drawings, the identical or equivalent portions to each other are designated by the same reference numerals and a description of such portions is simplified or omitted.

Embodiment

Configuration of PM Sensor According to Present Embodiment

Figure 2:
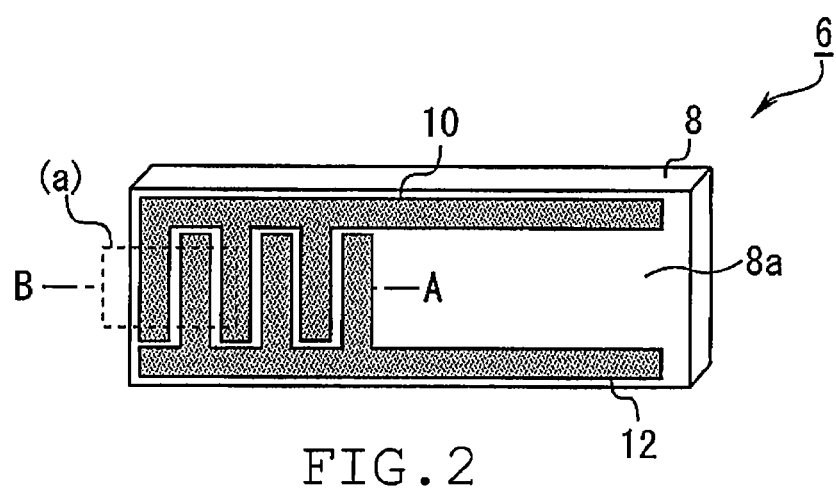
FIG. 2 is a diagram illustrating an element portion of the PM sensor according to the present embodiment of the present invention.

FIG. 1 and FIG. 2 are diagrams illustrating a PM sensor according to the present embodiment of the present invention. FIG. 1 shows overall configuration of the PM sensor and FIG. 2 shows enlarged view of part of an sensor element portion. The PM sensor shown in FIG. 1, for instance, is disposed downstream of a filter for trapping particulate matter (DPF; diesel particulate filter) in an exhaust passage of an internal combustion engine mounted on a vehicle and is used for detecting the amount of PM in exhaust gas.

As shown in FIG. 1, the PM sensor 2 includes a cover and an element portion 6 installed in a space in the cover 4. The cover 4 is provided with a plurality of holes. When the PM sensor 2 is used, exhaust gas flows into cover through the plurality of holes, and thus the element portion 6 is contacting with the exhaust gas.

As shown in FIG. 2, the element portion 6 of the PM sensor 2 includes an insulating substrate 8 (insulating body). The insulating substrate 8 is composed of alumina. A pair of electrodes 10, 12 is formed on a main surface 8a of the element portion 6. The electrodes 10, 12 are not in contact with each other as they are disposed at a fixed distance from each other. The electrodes 10, 12 each include a comb-tines-shaped portion. The comb-tines-shaped portions of the electrodes 10, 12 are disposed so that they mesh with each other. A heater (not shown) is embedded in an underlayer for the electrodes 10, 12 in the insulating substrate 8.

Distinguishing Configuration of PM Sensor According to Present Embodiment

Figure 3:
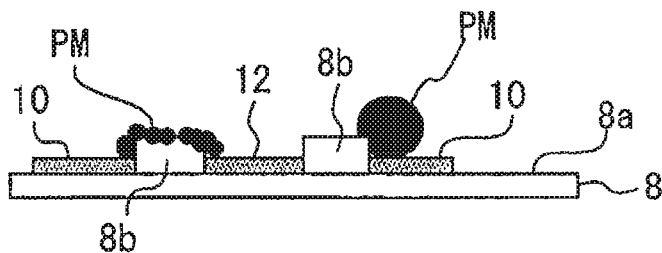
FIG. 3 is a diagram illustrating the cross-section configuration of the element portion of the PM sensor according to the present embodiment of the present invention.

FIG. 3 is a A-B cross-sectional view of the electrical portion 6 of PM sensor 2 according to present embodiment, in dashed line A of FIG. 2. In addition, FIG. 4 is a schematic view to explain a part of a conventional PM sensor equivalent to FIG. 3.

As shown in FIG. 3, in the PM sensor 2 according to present embodiment, an insulating portion 8b is formed on a part of main surface 8a of the insulating substrate 8, on which the electrodes 10, 12 are not formed. The insulating portion 8b is composed of sintered alumina which is same materials as the insulating substrate 8. In fact, the insulating portion 8b is disposed on an area of the main surface 8a sandwiched between the electrodes 10, 12. In a direction perpendicular to the main surface 8a of the element part 6 of the PM sensor 2, (i.e., in a direction from top to bottom in FIG. 3), the height of the surface of the electrodes 10, 12 is lower than the height of the surface of the insulating portion 8b.

Figure 4:
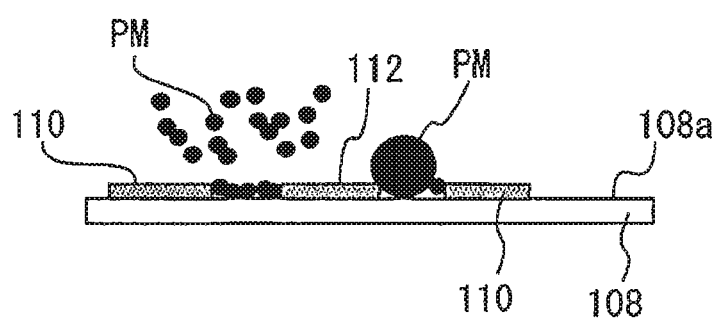
FIG. 4 is a diagram illustrating the cross-section configuration of an element portion of a conventional PM sensor.

On the other hand, in the conventional PM sensor shown in FIG. 4, a pair of electrodes 110, 112 having a comb-tines-shaped portion is formed on a main surface of an insulating substrate 108. However, an insulating portion is not formed on a part of the insulating substrate 108 where the electrodes 110, 112 are not formed. That is, a part between the pair of the electrodes 110, 112 is hollow in a direction perpendicular to a main surface 108a of an element portion, the main surface 108a of the insulating substrate 108 is exposed on the part between the pair of the electrodes 110, 112.

Method for Manufacturing PM Sensor According to Present Embodiment

The PM sensor 2 according to the present embodiment is produced by following method. First, an alumina base material composing the insulating substrate 8 is prepared, and an electrode pattern for forming the electrodes 10, 12 is printed on the alumina base material. Thereafter, mask material of same pattern as a pattern of the electrodes 10, 12 is printed on the electrode pattern. Here, material which vaporizes at a temperature equal to or lower than a sintering temperature of the electrodes is used as the mask material. Alumina thin film is formed on whole surface after forming the mask material. The alumina thin film and the electrode pattern sintered at high temperature after forming the alumina thin film, then the insulating portion 8b and the electrodes 10, 12 are formed. The mask material vaporizes in the course of sintering, therefore, the alumina thin film formed on the mask material is peeled. As a result, the insulating portion 8b which is composed of sintered alumina remains only on the part where the electrodes 10, 12 are not formed.

The peak diameter in a distribution of PM in exhaust gas is equal to or lower than about 100 nm. However, large PM having diameters more than several micrometer is irregularly generated in small quantity. In the conventional PM sensor, the large PM is interrupted by the electrodes 110, 112 formed convexly on the main surface 108a of the insulating substrate 108, and thus easily deposits on the main surface 108a being concave portions between the electrodes 110, 112 (Refer to FIG. 4). The large PM is likely to drastically change conductive property between the electrodes 110, 112. Therefore, in the conventional PM sensor, if large PM is generated, resistance between the electrodes 110, 112 is likely changed due to the large PM. AS a result, output of the conventional PM sensor different from real PM amount and variability in the output is likely to occur.

On the other hand, the PM sensor 2 according to the present embodiment has the insulating portion 8b more convex than the electrodes 10, 12, hence has no hollow between the electrodes 10, 12. Therefore, even if large PM is generated, PM are interrupted by the insulating portion 8b, and thus are likely to deposit on the electrodes 10, 12 (Refer to FIG. 3). Even if PM deposits on the electrodes 10, 12, it does not significantly influence conductive state between the electrodes 10, 12. More specifically, in the PM sensor 2 according to the present embodiment, if large PM is generated, variability in the output of the PM sensor 2 is difficult to occur and the PM sensor 2 is able to produce stable output, because large PM is difficult to deposit between the electrodes 10, 12.

Figure 5:
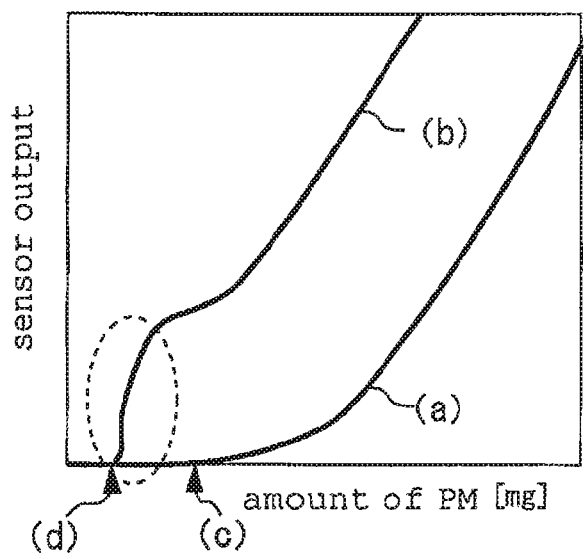
FIG. 5 is a diagram illustrating sensor output corresponding to the amount of PM of the PM sensor according to the present embodiment of the present invention, compared to output of a conventional PM sensor.

FIG. 5 is a diagram to make a comparative explanation about variations with amount of PM, in the output of the PM sensor according to the present embodiment and the output of the conventional PM sensor. In FIG. 5, the horizontal axis indicates the amount of PM, whereas the vertical axis indicates the outputs of the sensors. In FIG. 5, a curve (a) represents the output of the PM sensor 2 according to the present embodiment, whereas a curve (b) represents the output of the conventional sensor. In FIG. 5, (c) represents lower detection limit of the PM sensor according to the present embodiment 2, whereas (d) represents lower detection limit of the conventional PM sensor.

As shown in FIG. 5, the lower detection limit of the conventional PM sensor is small (Refer to (d)), and the conventional PM sensor is able to detect small amount of PM with high sensitivity. However, the output of the conventional PM sensor is likely to vary in condition of small amount of PM (Refer to (b)). On the other hand, the lower detection limit of the PM sensor 2 of the present embodiment is lager than that of the conventional sensor (Refer to (c)). However, the variability in the output of the PM sensor 2 is small and the PM sensor 2 is able to produce stable output according to PM amount (Refer to (a)).

Figure 6:
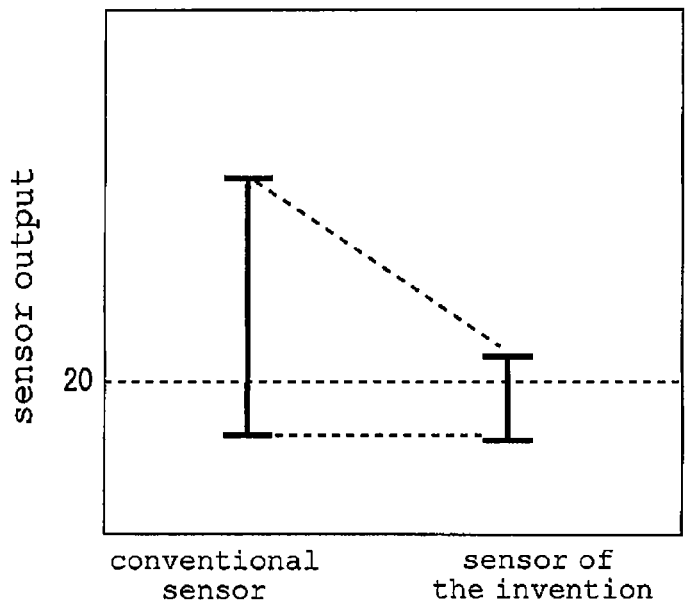
FIG. 6 is a diagram illustrating variability of the output of the PM sensor according to the present embodiment of the present invention, compared to that of a conventional PM sensor.

FIG. 6 is a diagram illustrating variability of the outputs of the PM sensor of the present embodiment and of the conventional sensor when measuring exhaust gas including PM amount of 20 mg as measured gas. Detection value based on the output of the conventional sensor is shown on the left side of plane paper of FIG. 6, whereas detection value based on the output of the PM sensor 2 according to the present embodiment is shown on the right side.

It is found that, for the same PM amount (20 mg), the detection value based on the sensor output of the conventional sensor varies in great range, whereas the variability of the sensor output of the PM sensor 2 of the present invention is reduced.

As described above, in the PM sensor 2 according to the present embodiment, the variability of the output is reduced by forming the insulation portion 8b between the electrodes 10, 12, and stable sensor output is achieved. However, the conductive pass with PM between the electrodes 10, 12 is difficult to be formed because the insulating portion 8b is an obstacle. Therefore, while the amount of PM depositing on the element portion 6 is small, the sensor output tends to be hard to appear. That is, improvement of the sensor sensitivity is in a relation of trade-off with reduction of the output variability by forming the convex insulating portion 8b.

Figure 7:
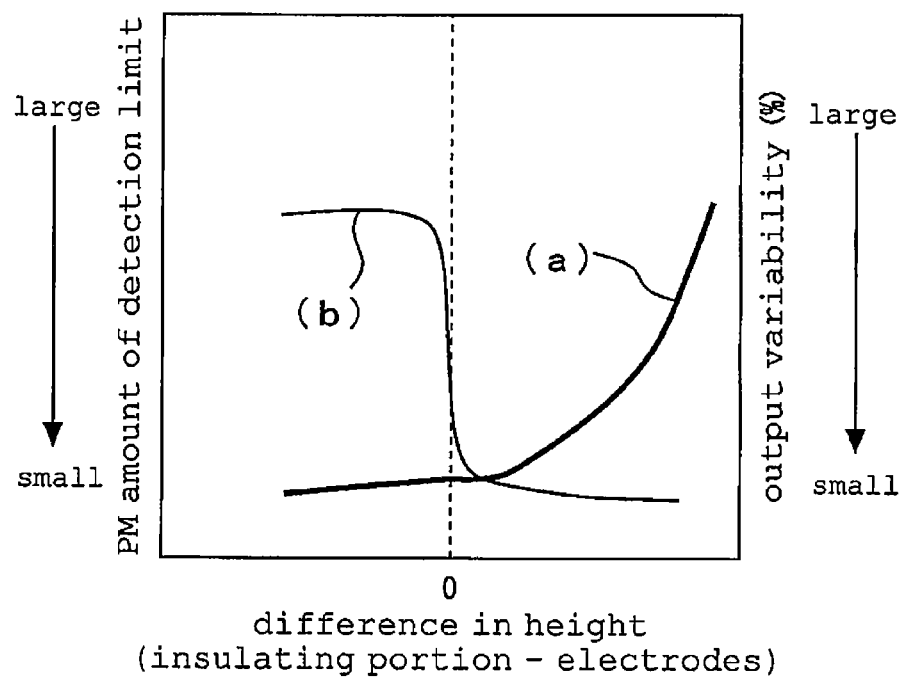
FIG. 7 is a diagram illustrating the variability of the output of the PM sensor or PM amount of detection limit in the present embodiment of the present invention, corresponding to difference in height between an electrode and an insulating portion of the PM sensor.

FIG. 7 is a diagram illustrating a relationship of the output variability and the PM amount of detection limit, corresponding to the difference in the height between the surfaces (i.e., the upper surfaces in FIG. 3) of electrodes 10, 12 and the insulating portions 8b. In FIG. 7, the horizontal axis indicates the difference in height between the portion between the electrodes 10, 12 (i.e., the insulating portion 8b), and the electrodes 10, 12. (That is, it is the difference between the surface of insulating portion and the surface of electrodes portion.) In the horizontal axis, the smaller value indicates the height of the electrodes 10, 12 is higher, whereas the larger the value indicates the height of the insulating portion 8b is higher. In FIG. 7, the vertical axis of the left side indicates the PM amount of detection limit, whereas the vertical axis of the right side indicates variability of detection. In FIG. 7, the curve (a) indicates the PM amount of detection limit, whereas the curve (b) indicates the variability of the detection.

As shown in (a) of FIG. 7, in the range in which the height of the surface of the electrodes 10, 12 is higher than that of the insulating portion 8b, (i.e., the range in which the difference in height in the horizontal axis is smaller than zero), the PM amount of detection limit is small. More specifically, the PM sensor is able to detect smaller amount of PM and have higher sensitivity. However, in the range in which the height of the electrodes 10, 12 is lower than that of the insulating portion 8b, (i.e., the range in which the difference in height is larger than zero), the PM amount of detection limit becomes larger with the difference in height being larger. More specifically, the sensor output is not achieved unless the much amount of PM deposits and the PM sensor has low sensitivity.

On the other hand, as shown by curve (b) in FIG. 7, in range where the height of the electrodes 10, 12 is higher than that of the insulating portion 8b, (i.e., the range in which the difference in height is smaller than zero), the variability of the detection is larger, whereas, in range where the height of the insulating portion 8b is higher than that of the electrodes 10, 12, the variability of the detection is smaller. Further, according to curve (b) of FIG. 7, the variability of the detection suddenly changes in the vicinity of the difference in height zero area, in which the heights of surfaces of the electrodes 10, 12 and the insulating portion 8b are identical. Therefore, it is considered that the variability of the output is largely improved by forming the electrodes 10, 12 so as to be slightly lower than the insulating portion 8b.

On the basis of the above predisposition, in consideration of tolerance of detection variability and intended sensor sensitivity, the height of the insulation portion 8b and the height of the electrodes 10, 12 are decided appropriately. As described above, the PM amount of the detection limit becomes, in range where the difference in height is larger than zero, larger with the difference in height being larger, whereas the variability of the detection drastically changes in vicinity of the difference in height zero area and becomes larger in the range where the insulation portion is larger (i.e., the range in which the difference in height is smaller than zero). Therefore, the difference in height is preferably set in tiny positive (that is, the insulating portion 8b is higher) value. In the present invention, the heights of the surfaces of the insulating portion 8b and the electrodes 10, 12 may be identical (that is, the difference in height may be zero).

In addition, in the present embodiment, the method for manufacturing the PM sensor 2 was described. However, the method for manufacturing a PM sensor of this invention is not limited to this. The other methods may be accepted. More specifically, an electrode pattern, a mask or an alumina film is not formed by a printing method but may be formed by the method that is suitable for materials to be used for each of them, such as a vapor deposition method, a sputtering method and a CVD method and the like. Further, the manufacturing method is not limited to the above. The trench of the same configuration of an electrode pattern may be formed in an alumina base material as the insulation substrate, and then, an electrode may be buried in the bottom of the trench by a printing method or the other methods. In this case, the difference in height between the surface of the portion composing the insulating portion 8b (i.e., the portion of the alumina base material where the trench does not formed) and the surface of the electrodes 10, 12 is accommodated by accommodating the depth of the formed trench and the thickness of the electrodes.

The present embodiment has also been described on the assumption that the insulating portion 8b which is convex more than the electrodes 10, 12 is formed on whole portion where the electrodes 10, 12 are not formed in the main surface 8a. However, the present invention is not limited to this. The configuration that an insulating portion which is equal to or higher than the electrodes 10, 12 is formed only on the comb-tines-shaped portions of the electrodes 10, 12 may be adopted. The PM sensor 2 emits an output depending on the amount of PM depositing between the electrodes 10, 12, specifically between the comb-tine shaped portions of electrodes 10, 12. Therefore, if an insulating portion which is convex more than the electrodes 10, 12 is formed only on the comb-tines shaped portions of the electrodes 10, 12, the variability of the output due to deposition of large PM is suppressed.

The present embodiment has also been described on the assumption that alumina is used as constitution materials of the insulating substrate 8 and the insulating portion 8b. However, in this invention, the constitution materials of the insulating body are not limited to alumina. Insulating materials having high heat-resistance is preferably used as the insulating body. Specifically, for example, silicon carbide, cordierite, alumina titanate, sialon, mullite, silicon nitride, zirconium phosphate, zirconia, titania, alumina, and silica, ceramics composed of combination thereof, and material primarily composed of sintered metal are suitable as material of the insulating body.

In the present invention, material composing the electrodes 10, 12 is not limited. For example, transition metal such as Pt, Rh, Pd, Ag, Au and Ir, alloyed material including any of these transition elements, and complex material containing a sensor ceramic including any of these transition elements are suitable as material of the electrodes 10, 12.

When the number, quantity, amount, range, or other numerical attribute of an element is mentioned in the above description of the embodiment, the present invention is not limited to the mentioned numerical attribute unless it is unequivocally stated or theoretically defined. Further, structures and steps of methods described in connection with the embodiment are not necessarily essential to the present invention unless they are unequivocally stated or theoretically defined.

DESCRIPTION OF NOTATIONS

2 sensor
6 element portion
8 insulating substrate
8a main surface
8b insulating portion
10, 12 electrode

The invention claimed is:

1. A particulate matter sensor to detect particulate matter in a gas to be measured, the particulate matter sensor comprising:
    a cover including a plurality of holes, the cover located in a path of the gas;
    an insulating body inside the cover; and
    a pair of electrodes which is disposed on a main surface of the insulating body and positioned apart from each other;
    wherein the insulating body includes, on a part of the main surface which is sandwiched between the pair of the electrodes and where the pair of the electrodes is not formed, an insulating portion being higher than the pair of the electrodes in a direction perpendicular to the main surface, and
    wherein a difference between a height of a surface of the electrodes and a height of a surface of the insulating portion is less than half of a distance between midpoints of two adjacent electrodes.

2. A method to manufacture the particulate matter sensor according to claim 1, comprising:
    forming an electrode pattern composed of material for the pair of the electrodes on a base material composing the insulating body;
    forming, after forming the electrode pattern, on the electrode pattern, a mask including a pattern identical to the electrode pattern and composed of material which vaporizes at a temperature equal to or lower than a temperature at which the electrode pattern is sintered;
    forming a thin film composed of material for the insulating portion on the mask and the base material;
    sintering the electrode pattern and the thin film to form the electrodes and the insulating portion.

3. A method to manufacture the particulate matter sensor according to claim 1, comprising:
    forming a trench including a configuration identical to a pattern of the pair of the electrodes on a base material composing the insulating body;
    forming the pair of the electrodes on a bottom of the trench.

4. The particulate matter sensor according to claim 1, wherein:
    the pair of the electrodes includes comb-tines-shaped portions disposed so that the comb-tines-shaped portions mesh with each other in a state of being not in contact with each other; and
    the insulating portion is disposed at least on a part sandwiched between the comb-tines-shaped portions of the pair of the electrodes.

* * * * *